United States Patent [19]

Yoshioka et al.

[11] Patent Number: 4,709,065
[45] Date of Patent: Nov. 24, 1987

[54] ORGANOSILICON COMPOUND HAVING POLYSULFIDE LINKAGES AND A RUBBER COMPOSITION COMPRISING THE SAME

[75] Inventors: Hiroshi Yoshioka; Ichiro Ono, both of Annaka; Hitoshi Uehara, Matsuida, all of Japan

[73] Assignee: Shin-Etsu Chemical Co., Ltd., Tokyo, Japan

[21] Appl. No.: 909,783

[22] Filed: Sep. 19, 1986

[30] Foreign Application Priority Data

Sep. 20, 1985 [JP] Japan .................... 60-208292

[51] Int. Cl.⁴ .................... C07F 7/08; C07F 7/18
[52] U.S. Cl. .................................................. 556/428
[58] Field of Search ........................................ 556/428

[56] References Cited

U.S. PATENT DOCUMENTS

| | | | |
|---|---|---|---|
| 3,317,461 | 5/1967 | Plueddemann | 556/428 X |
| 3,842,111 | 10/1974 | Meyer-Simon et al. | 556/428 |
| 3,873,489 | 3/1975 | Thurn et al. | 556/428 X |
| 3,946,059 | 3/1976 | Janssen et al. | 556/428 |
| 3,978,103 | 8/1976 | Meyer-Simon et al. | 556/428 |
| 4,129,585 | 12/1978 | Buder et al. | 556/428 |
| 4,681,961 | 7/1987 | Zerpner et al. | 556/428 |

*Primary Examiner*—Paul F. Shaver
*Attorney, Agent, or Firm*—Hopgood, Calimafde, Kalil, Blaustein & Judlowe

[57] ABSTRACT

The novel organosilicon compound of the invention has two polysulfide linkages in a molecule and is represented by the general formula

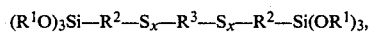

in which $R^1$ is an alkyl group having from 1 to 4 carbon atoms, $R^2$ is a divalent hydrocarbon group having from 1 to 10 carbon atoms, $R^3$ is a divalent hydrocarbon group having from 2 to 10 carbon atoms or a divalent hydrocarbon group additionally containing one or more of the linking units of the formula —O— or —CO—O— in the structure and X is a positive integer of from 2 to 6. The compound is useful as an additive in a rubber composition based on natural rubber or a diene-based synthetic rubber and a non-carbon inorganic filler to greatly improve the mechanical properties of the vulcanizate without increasing the Mooney viscosity of the unvulcanized rubber composition.

7 Claims, 3 Drawing Figures

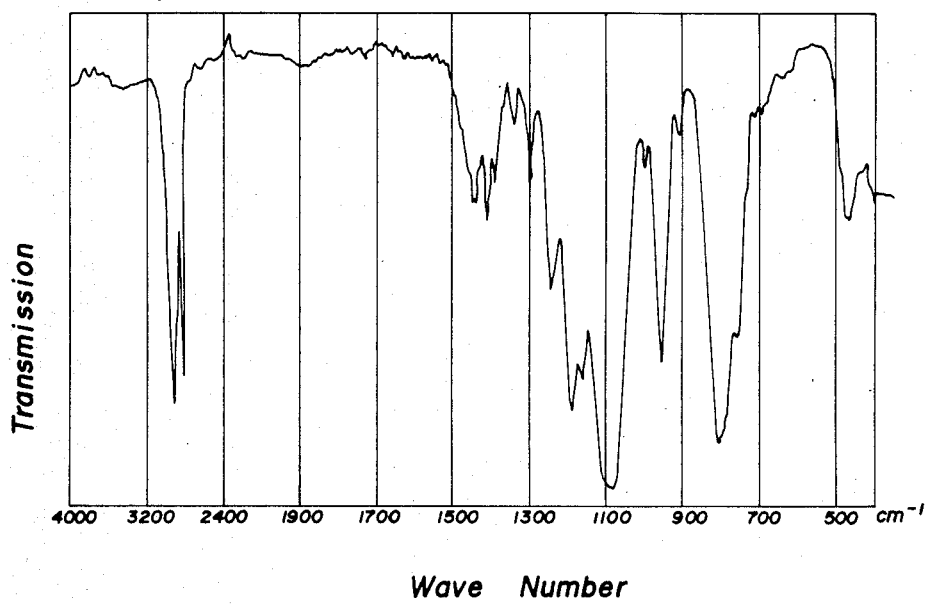

ORGANOSILICON COMPOUND HAVING POLYSULFIDE LINKAGES AND A RUBBER COMPOSITION COMPRISING THE SAME

BACKGROUND OF THE INVENTION

The present invention relates to a novel organosilicon compound having two polysulfide linkages in a molecule not known in the prior art and not described in any literatures and a method for the preparation thereof as well as a rubber composition comprising the novel organosilicon compound. More particularly, the invention relates to the above mentioned novel organosilicon compound and the method for the preparation thereof as well as a rubber composition comprising natural rubber or a diene-based synthetic rubber, a non-carbon inorganic filler and the organosilicon compound as a modifying agent of the properties of the rubber vulcanizates.

In comparison with a rubber composition formulated with a carbon black filler, as is well known, rubber compositions based on natural rubber or a diene-based synthetic rubber and formulated with a non-carbon inorganic filler are inferior in respect of the poor processibility of the unvulcanized rubber composition and the low mechanical properties of the vulcanizates thereof such as tensile strength, tear strength, elastic modulus, stress-strain characteristics, elastic resilience and anti-wearing resistance because the inorganic filler inherently has no affinity with the polymeric rubbery constituent and exhibits no reinforcing effect as a result of formation of the so-called carbon gel formed in the rubber compositions loaded with a carbon black filler.

Various proposals and attempts have been made hitherto to achieve an improvement of rubber compositions in this regard. One of the promising ways for the improvement in the prior art is to blend the rubber composition with an organosilicon compound having a polysulfide linkage in a molecule. For example, Japanese Patent Publication No. 51-28623 and Japanese Patent Kokai 52-83527 teach that the rubber composition may be admixed with an organosilicon compound represented by the general formula (RO)$_3$Si—R'—S$_x$—R'—Si(OR)$_3$ or
[(X)$_3$—y(R)ySi—R'$_n$—Ar]$_a$[S$_x$]$_b$, in which R is a monovalent hydrocarbon group, R' is a divalent hydrocarbon group, Ar is an aryl group, X is a hydrolyzable group, x is a positive integer of 2 to 6, y is zero, 1 or 2, n is zero or 1 and a and b are each a positive integer of at least 2 and at least 1 with the proviso that the ratio a:b is in the range from 0.4 to 2.

This method is indeed effective and substantial improvements can be obtained in the rubber vulcanizates of the compositions formulated with such an organosilicon compound relative to the tensile strength, tear strength, elastic modulus and stress-strain characteristics. The degree of improvements achieved by this method, however, is still insufficient in respect of the anti-wearing resistance and the mechanical properties of the vulcanizates at elevated temperatures. Accordingly, it has been eagerly desired to develop a novel additive compound capable of fully improving the rubber compositions without the above mentioned problems in the prior art additive compounds. The inventors have continued extensive investigations to discover an organosilicon compound having a polysulfide linkage and useful for the purpose and arrived at the completion of the present invention.

SUMMARY OF THE INVENTION

Thus, the novel organosilicon compound discovered as a result of the inventors' investigations and useful as an additive in a rubber composition is a compound represented by the general formula

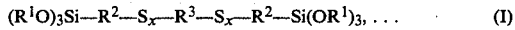

$(R^1O)_3Si-R^2-S_x-R^3-S_x-R^2-Si(OR^1)_3,\ldots$ (I)

in which $R^1$ is an alkyl group having from 1 to 4 carbon atoms, $R^2$ is a divalent hydrocarbon group having from 1 to 10 carbon atoms, $R^3$ is a divalent hydrocarbon group having from 2 to 10 carbon atoms and optionally containing one or more of the linking units of the formula —O— or —CO—O— in the structure and x is a positive integer of from 2 to 6. The method for the preparation of such an organosilicon compound will be described later in detail.

The above defined novel organosilicon compound having two polysulfide linkages in a molecule may serve as an additive of a rubber composition capable of giving a vulcanizate having remarkably improved mechanical properties.

Thus the rubber composition of the invention comprises:

(a) 100 parts by weight of natural rubber or a diene-based synthetic rubber;

(b) from 5 to 200 parts by weight of a non-carbon inorganic filler; and (c) from 0.1 to 20 parts by weight of the above described novel organosilicon compound having two polysulfide linkages in a molecule.

BRIEF DESCRIPTION OF THE DRAWING

FIGS. 1, 2 and 3 each illustrate an infrared absorption spectrum of the organosilicon compound having two polysulfide linkages in a molecule prepared in Examples 1, 2 or 3, respectively.

DETAILED DESCRIPTION OF THE PREFERRED EMBODIMENTS

Figure 1:
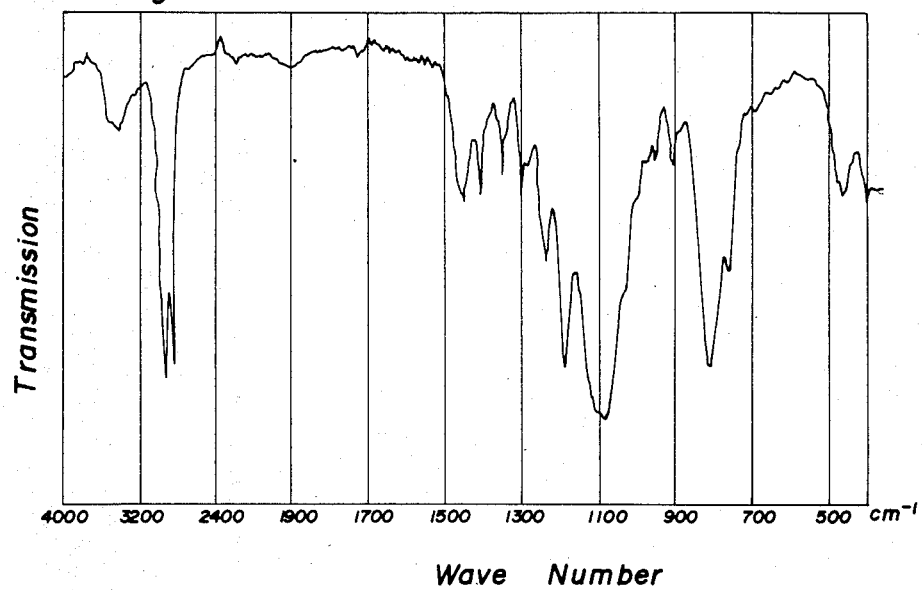

The novel organosilicon compound provided by the present invention is represented by the above given general formula (I). In the formula, $R^1$ is an alkyl group having from 1 to 4 carbon atoms including methyl, ethyl, propyl and butyl groups. The group $R^1$ is bonded to the silicon atom always through an oxygen atom or in the form of an alkoxy group to form a trialkoxysilyl group at each molecular chain end. The group denoted by $R^1$ is preferably a methyl or an ethyl group giving a relatively large velocity of hydrolysis to the alkoxy groups in view of the role played by the alkoxy groups that they are readily hydrolyzed by the water contained in the rubber composition, which sometimes originates in the inorganic filler in the form of adsorbed water or water of crystallization, to be converted into silanol groups which are adsorbed on the filler particles and act as a coupling agent between the filler particles and the polymeric rubber matrix to contribute to the improvements of the properties of the rubber vulcanizates.

The group denoted by the symbol $R^2$ is a linking unit between the above mentioned trialkoxysilyl group and one of the polysulfide linkages and is a divalent hydrocarbon group having from 1 to 10 carbon atoms. Exemplary of the divalent hydrocarbon groups denoted by $R^2$ are those expressed by the following formulas:

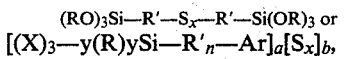

—CH$_2$—;  —CH$_2$CH$_2$—;  —CH$_2$CH$_2$CH$_2$—; —CH$_2$CH$_2$CH$_2$CH$_2$—; —CH$_2$CH(CH$_3$)CH$_2$—; —C$_6$H$_4$—, i.e. a phenylene group; —CH$_2$C$_2$CH$_6$—H$_4$—CH$_2$—; and the like. The group denoted by the symbol R$^3$ is a unit linking the two polysulfide linkages and is a divalent hydrocarbon group having from 2 to 10 carbon atoms and optionally containing one or more of the linking units of the formula —O— or —CO—O— in the structure. Exemplary of the divalent group denoted by R$^3$ are those expressed by the following formulas:

—CH$_2$CH$_2$—; —CH$_2$CH$_2$CH$_2$; —CH$_2$CH$_2$CH$_2$CH$_2$; CH$_2$CH=CHCH$_2$—;
—CH$_2$CH$_2$CH$_2$CH$_2$CH$_2$—; —CH$_2$CH$_2$——CH$_2$CH$_2$—; —CH$_2$CH$_2$—O—CH$_2$CH$_2$CH$_2$—;
—CH$_2$CH$_2$—0—CH$_2$CH$_2$—O—CH$_2$CH$_2$—;
—CH$_2$CH$_2$CH$_2$—O—CH$_2$CH$_2$CH$_2$—O—CH$_2$CH$_2$CH$_2$—;
—CH$_2$CH$_2$—CO—O—CH$_2$CH$_2$—O—CO—CH$_2$CH$_2$—;
—CH$_2$CH$_2$—CO—O—CH$_2$CH$_2$CH$_2$—O—CO—CH$_2$CH$_2$—;

and the like. The subscript x is a positive integer of 2 to 6 or, typically, 4 although it is a rather difficult matter to synthetically obtain the organosilicon compound of which all of the molecules have the tetrasulfide linkages alone with x equal to 4 more or less containing other molecular species of which the value of x ranges between 2 and 6.

Exemplary of the inventive novel organosilicon compound having two polysulfide linkages in a molecule are those expressed by the following structural formulas:

(CH$_3$O)$_3$Si—C$_3$H$_6$S$_4$C$_2$H$_4$—O—C$_2$H$_4$—O—C$_2$H$_4$S$_4$C$_3$H$_6$—Si(OCH$_3$)$_3$;
(CH$_3$O)$_3$Si—C$_3$H$_6$S$_4$C$_2$H$_4$—CO—O—C$_2$H$_4$—O—CO—C$_2$H$_4$S$_4$C$_3$H$_6$—Si(OCH$_3$)$_3$;
(C$_2$H$_5$O)$_3$Si—C$_3$H$_6$S$_4$CH$_2$CH=CHCH$_2$S$_4$C$_3$H$_6$—Si(OC$_2$H$_5$)$_3$;
(CH$_3$O)$_3$Si—C$_3$H$_6$S$_4$C$_4$H$_8$S$_4$C$_3$H$_6$—Si(OCH$_3$)$_3$;
(C$_2$H$_5$O)$_3$Si—C$_2$H$_4$S$_4$C$_5$H$_{10}$S$_4$C$_2$H$_4$—Si(OC$_2$H$_5$)$_3$;
(C$_2$H$_5$O)$_3$Si—CH$_2$S$_4$C$_2$H$_4$—O—C$_2$H$_4$S$_4$CH$_2$—Si(OC$_2$H$_5$)$_3$;
(CH$_3$O)$_3$Si—CH$_2$CH(CH$_3$)CH$_2$S$_4$C$_3$H$_6$—O—C$_3$H$_6$S$_4$CH$_3$CH(CH$_3$)CH$_2$—Si(OCH$_3$)$_3$;
(C$_2$H$_5$O)$_3$Si—C$_3$H$_6$S$_4$CH$_2$—CO—O—C$_2$H$_4$—O—CO—CH$_2$S$_4$C$_3$H$_6$—Si(OC$_2$H$_5$)$_3$;
(CH$_3$O)$_3$Si—C$_6$H$_4$S$_4$CH$_2$CH=CHCH$_2$S$_4$C$_6$H$_4$—Si(OCH$_3$)$_3$;
(C$_2$H$_5$O)$_3$Si—C$_2$H$_4$C$_6$H$_4$CH$_2$S$_4$C$_3$H$_6$—O—C$_3$H$_6$——C$_3$H$_6$S$_4$CH$_2$C$_6$H$_4$C$_2$H$_4$—Si(OC$_2$H$_5$)$_3$;
(CH$_3$O)$_3$Si—C$_2$H$_4$C$_6$H$_4$CH$_2$S$_4$C$_2$H$_4$—CO—O—C$_4$H$_8$—O—CO——C$_2$H$_4$S$_4$CH$_2$C$_6$H$_4$C$_2$H$_4$—Si(OCH$_3$)$_3$; and
(CH$_3$O)$_3$Si—C$_6$H$_4$S$_4$C$_2$H$_4$S$_4$C$_6$H$_4$—Si(OCH$_3$)$_3$.

The organosilicon compound of the invention can be prepared in several different synthetic routes. One of the convenient synthetic methods therefor is performed by first reacting a mercaptoalkyl trialkoxy silane of the formula (R$^1$O):$_3$SiR$^2$SH with sulfur chloride in the presence of an acceptor for hydrogen chloride such as triethyl amine to give a compound of the formula (R$^1$O)$_3$SiR$^2$S$_{x-1}$Cl by the dehydrochlorination reaction and this compound is further subjected to another dehydrochlorination reaction with a dimercaptan compound of the formula HS—R$^3$—SH to give the desired compound of the general formula (I). Alternatively, a chloroalkyl trialkoxy silane of the formula (R$^1$O)$_3$SiR$^2$Cl is first reacted with sodium sulfide of the formula Na$_2$S$_x$ to form a compound of the formula (R$^1$O)$_3$SiR$^2$S$_x$Na which is further reacted with a dihalide compound of the formula X—R$^3$—X, in which X is a halogen atom, to give the desired compound of the general formula (I).

Although the inventive organosilicon compound has a possibility of being useful in a variety of applications, the most prominent advantage is obtained when the compound is used as an additive in a rubber composition comprising natural rubber or a diene-based synthetic rubber and a non-carbon inorganic filler to greatly improve the mechanical properties of the vulcanizate without increase or rather with decrease in the Mooney viscosity of the unvulcanized rubber composition. Namely, the present invention further relates to a rubber composition comprising (a) natural rubber or a diene-based synthetic rubber, (b) a non-carbon inorganic filler and (c) the above described novel organosilicon compound having two polysulfide linkages in a molecule. It is presumable that the alkoxysilyl groups of the formula (R$^1$O)$_3$Si— in the organosilicon compound added to the rubber composition are firmly bonded to the surface of the filler particles by physical adsorption or chemical bonding so that the Mooney viscosity of the unvulcanized rubber composition is decreased to improve the processibility or workability of the composition. When the rubber composition is vulcanized in the presence of a vulcanizing agent such as sulfur, the polysulfide linkages in the organosilicon compound are chemically bonded to the molecules of the rubbery polymer to finally serve as a linking units between the rubber molecules and the filler particles to contribute to the improvements of the mechanical properties of the vulcanizates including the tensile strength, tear strength, elastic modulus and stress-strain characteristics as well as the anti-wearing resistance and various mechanical properties at elevated temperatures.

The rubbery polymer as the base ingredient of the inventive rubber composition is natural rubber or a diene-based synthetic rubber exemplified by copolymeric rubbers of styrene and butadiene, polybutadiene rubbers, polyisoprene rubbers, copolymeric rubbers of acrylonitrile and butadiene, terpolymeric rubbers of ethylene, propylene and a diene monomer, polychloroprene rubbers, bromo- or chlorobutylene rubbers and the like. These rubbers can be used either singly or as a combination of two kinds or more according to need.

The non-carbon inorganic filler compounded with the rubbery polymer can be any of known ones exemplified by siliceopus powders such as finely divided silica fillers, e.g. precipitated and fumed silica fillers and silica aerogel, and finely pulverized quartz, finely divided glassy materials such as glass powders, glass beads and glass fibers, metal silicates such as calcium silicate, magnesium silicate and aluminum silicate and metal oxides such as aluminum oxide, titanium dioxide and zinc oxide, of which the first mentioned siliceous powders give the best results. The amount of the inorganic filler compounded with the rubbery polymer should be in the range from 5 to 200 parts by weight or, preferably, from 5 to 100 parts by weight per 100 parts by weight of the rubbery polymer as the component (a). When the amount of the filler is too small, no reinforcing effect can be obtained while a rubber composition compounded with a too large amount of the filler may be poorly processible or workable due to the unduly increased consistency.

The amount of the novel organosilicon compound added to the rubber composition as the component (b) should be in the range from 0.1 to 20 parts by weight or, preferably, from 0.5 to 10 parts by weight per 100 parts by weight of the rubbery polymer as the component (a). When the amount thereof is too small, the desired effect of improvement in the mechanical properties of the rubber vulcanizates can hardly be obtained as a matter of course while addition of a too large amount of the compound has no particular additional advantages rather with certain adverse influences on the elongation and flexiblity of the vulcanizates if not to mention the economical disadvantage due to the expensiveness of the organosilicon compound.

The inventive rubber composition can be obtained by merely blending the components (a), (b) and (c) together with other optional ingredients. Conveniently, the organo-silicon compound may be first diluted with a process oil before compounding with the components (a) and (b) or the inorganic filler is treated beforehand with the organo-silicon compound and then compounded with rubbery polymer as the component (a) in order to ensure good dispersibility of the filler in the rubbery matrix. For example, the organo-silicon compound is diluted with an aqueous alcohol containing up to 20% by weight of water and the inorganic filler is blended with the solution followed by evaporation of the solvents to give a filler surface-treated with the organosilicon compound. The amount of the organosilicon compound in this surface treatment of the inorganic filler should be in the range from 0.1 to 20 parts by weight or, preferably, from 0.5 to 10 parts by weight per 100 parts by weight of the filler.

The rubber composition of the invention should contain a vulcanizing agent which is preferably sulfur used in an amount of about 0.1 to 4 parts by weight per 100 parts by weight of the rubbery polymer as combined with about 2 to 5 parts by weight of zinc oxide and about 0.2 to 5 parts by weight of a vulcanization accelerator. Various kinds of vulcanization accelerators can be used including thiourea-based ones, guanidine-based ones, thiazole-based ones, sulfenamide-based ones, dithiocarbamate-based ones, thiuram-based ones and xantogenic acid-based ones. Other optional additives to the rubber composition include aging retarders, antioxidants, process oils, plasticizers, body pigments, carbon black, vulcanization retarders, coloring agents and the like.

In the following, the present invention is described in more detail by way of examples including description of the preparation of the inventive novel organosilicon compounds and rubber compositions compounded therewith. Hereinbelow, the expression of "parts" always refers to "parts by weight" and the values of viscosity are all those obtained by the measurement at 25° C.

EXAMPLE 1

Into a glass-made flask of 1 liter capacity equipped with a stirrer, reflux condenser, thermometer and dropping funnel were introduced 135 g (1 mole) of sulfur chloride and 600 g of n-hexane to form a reaction mixture into which 196 g (1 mole) of 3-mercaptopropyl trimethoxy silane were added dropwise over a period of 2 hours with agitation. As the silane was added, hydrogen chloride gas was evolved from the reaction mixture in the flask exothermically to increase the temperature of the reaction mixture to 43° C. After completion of the dropwise addition of the silane compound, the mixture was heated and kept at 60° C. under bubbling of dry nitrogen gas thereinto for 3 hours to complete the reaction along with removal of the hydrogen chloride remaining in the mixture followed by cooling to 20° C.

Thereafter, 91 g (0.5 mole) of triethylenglycol dimercaptan were added dropwise into the reaction mixture under agitation in the flask over a period of 30 minutes so that the temperature of the mixture was increased to 48° C. by the exothermic reaction. After completion of the dropwise addition of the triethyleneglycol dimercaptan, heating of the reaction mixture was continued for further 3 hours under reflux of n-hexane to complete the reaction followed by the addition of 95 g of triethylamine to neutralize residual hydrogen chloride and filtration of the mixture to remove the precipitated triethylamine hydrochloride. Stripping of the n-hexane from the filtrate solution by distillation gave 302 g of a yellow liquid as the product having a viscosity of 104 centistokes, specific gravity of 1.25 and refractive index of 1.557.

The results of the infrared absorption spectrometric and elementary analyses supported that this product was a tetrasulfide linkage-containing organosilicon compound of the formula (CH$_3$O)$_3$Si—C$_3$H$_6$S$_4$C$_2$H$_4$—O—C$_2$H$_4$—O—C$_2$H$_4$S$_4$C$_3$H$_6$—Si(OCH$_3$)$_3$.

An infrared spectrum of this organosilicon compound is shown in FIG. 1 and the results of the elementary analysis were as follows.

|  | C, % | H, % | Si, % | S, % |
|---|---|---|---|---|
| Calculated as C$_{18}$H$_{42}$O$_8$S$_8$Si$_2$ | 30.92 | 6.05 | 8.03 | 36.69 |
| Found | 30.94 | 6.03 | 7.98 | 36.75 |

EXAMPLE 2

The synthetic procedure was substantially the same as in Example 1 except that 119 g (0.5 mole) of ethyleneglycol di($\beta$-mercaptopropionate) HSC$_2$H$_4$CO—O—C$_2$H$_4$—O—COC$_2$H$_4$SH were used instead of 91 g of triethyleneglycol dimercaptan and the amount of triethylamine was increased to 98 g to give 324 g of a yellow liquid product having a viscosity of 141 centistokes, specific gravity of 1.29 and refractive index of 1.554.

The results of the infrared absorption spectrometric and elementary analyses supported that this product was a tetrasulfide linkage-containing organosilicon compound of the formula (CH$_3$O)$_3$Si—C$_3$H$_6$S$_4$C$_2$H$_4$—CO—O—C$_2$H$_4$—O—CO—C$_2$H$_4$S$_4$H$_6$—Si(OCH$_3$)$_3$.

Figure 2:
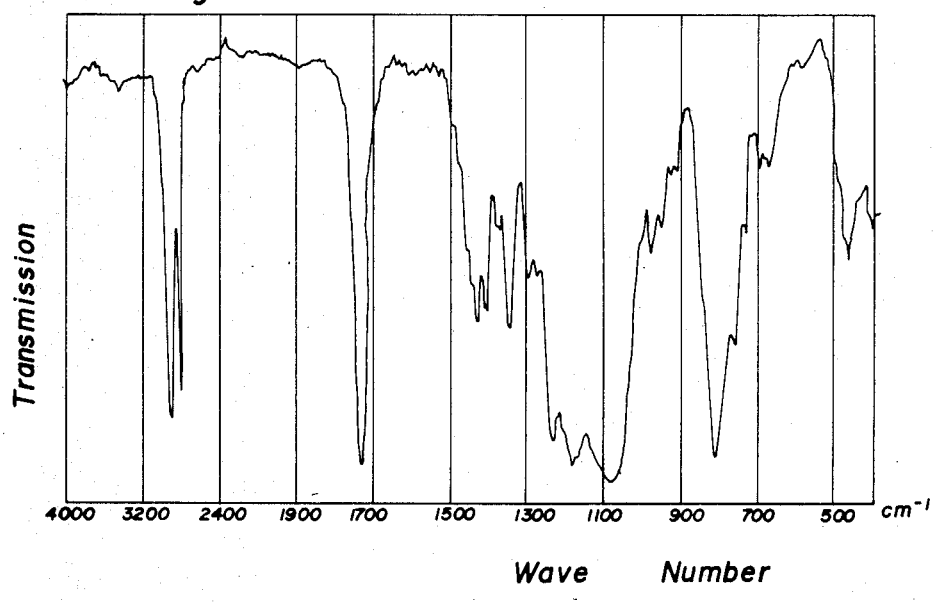

An infrared spectrum of this organosilicon compound is shown in FIG. 2 and the results of the elementary analysis were as follows.

|  | C, % | H, % | Si, % | S, % |
|---|---|---|---|---|
| Calculated as C$_{20}$H$_{42}$O$_{10}$S$_8$Si$_2$ | 29.57 | 5.79 | 7.68 | 35.08 |
| Found | 29.55 | 5.80 | 7.66 | 35.13 |

EXAMPLE 3

Into the same glass-made reaction vessel as used in Example 1 were introduced 174 g (1 mole) of sodium sulfide Na$_2$S$_4$ and 500 g of anhydrous ethyl alcohol to form a reaction mixture and 240.5 g (1 mole) of 3-chloropropyl triethoxy silane were added dropwise over a period of 45 minutes into the reaction mixture under agitation in the reaction vessel kept at 60° C. on a hot water bath. As the silane was added, the temperature of the reaction mixture was increased up to 78° C. by the exothermic reaction. After completion of the dropwise addition of the silane compound, the mixture was heated for further 3 hours under reflux of ethyl alcohol to complete the reaction followed by dropwise addition of 62.5 g (0.5 mole) of 1,4-dichloro-2-butene over a period of 30 minutes and the reaction mixture was heated for further 5 hours under reflux of ethyl alcohol to complete the reaction. After cooling to room temperature, the reaction mixture was filtered to remove the precipitated sodium chloride. Stripping of the ethyl alcohol from the filtrate solution by distillation gave 310 g of a yellow liquid as the product having a viscosity of 53 centistokes, specific gravity of 1.22 and refractive index of 1.559.

The results of the infrared absorption spectrometric and elementary analyses supported that this product was a tetrasulfide linkage-containing organosilicon compound of the formula $(C_2H_5O)_3Si\text{—}C_3H_6S_4CH_2CH\text{=}CHCH_2S_4C_3H_6\text{—}Si(OC_2H_5)_3$.

An infrared spectrum of this organosilicon compound is shown in FIG. 3 and the results of the elementary analysis were as follows.

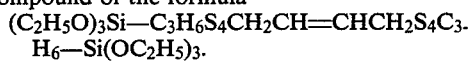

|  | C, % | H, % | Si, % | S, % |
|---|---|---|---|---|
| Calculated as $C_{22}H_{48}O_6S_8Si_2$ | 36.63 | 6.71 | 7.79 | 35.56 |
| Found | 36.57 | 6.70 | 7.81 | 35.61 |

EXAMPLE 4

Five rubber compositions, referred to as the rubber compositions No. 1 to No. 5, were prepared each by uniformly blending, on a 6-inch roller mill, 100 parts of natural rubber No. III, 50 parts of a precipitated silica filler (Nipsil AQ, a product by Nippon Silica Co.), 2 parts of sulfur, 10 parts of a process oil (Aroma 790, a product by Nippon Sun Oil Co.), 5 parts of zinc oxide, 0.5 part of diphenyl guanidine, 0.5 part of 2-mercaptobenzothiazole and 0.5 part of N-hydroxydiethylene-2-benzothiazole sulfenamide. The rubber compositions No. 1, No. 2 and No. 3 were each further admixed with 2 parts of the tetrasulfide linkage-containing organosilicon compounds prepared in Examples 1, 2 and 3, respectively, while the rubber composition No. 5 was admixed with 2 parts of a tetrasulfide linkage-containing organosilicon compound of the formula $(C_2H_5O)_3SiCH_2CH_2CH_2S_4CH_2CH_2CH_2Si(OC_2H_5)_3$,

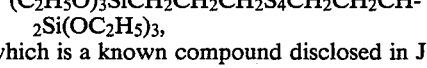

which is a known compound disclosed in Japanese Patent Publication No. 51-28623. The rubber composition No. 4 was not admixed with such a tetrasulfide linkage-containing organosilicon compound.

These rubber compositions before vulcanization were subjected to the measurement of the Mooney viscosity to give the results shown in Table 1 below. Further, the rubber compositions were each vulcanized by heating at 160° C. for 20 minutes and various mechanical properties were determined of the vulcanizates to give the results shown in Table 1. The Akron abrasion test appearing at the bottom line of the table was undertaken according to British Standard 903 A-9 (1957) at an angle of abrasion of 25° using a reference specimen prepared from a rubber composition formulated with 100 parts of natural rubber No. III, 50 parts of carbon black ISAF, 10 parts of a process oil, 5 parts of zinc oxide, 2 parts of stearic acid, 0.5 part of dibenzothiazolyl sulfide, 0.5 part of N-hydroxydiethylene-2-benzothiazole sulfenamide and 2 parts of sulfur.

TABLE 1

| Rubber composition No. | 1 | 2 | 3 | 4 | 5 |
|---|---|---|---|---|---|
| Mooney viscosity $ML_{1+4}$, minutes | 31 | 30 | 40 | 68 | 43 |
| Hardness, JIS | 52 | 52 | 52 | 46 | 52 |
| Ultimate elongation, % | 565 | 543 | 548 | 660 | 538 |
| Tensile strength, kg/cm$^2$ | 101 | 105 | 98 | 55 | 82 |
| Tear strength, kg/cm | 29 | 31 | 30 | 18 | 26 |
| Elastic modulus at 100%, kg/cm$^2$ | 14 | 14 | 15 | 8 | 13 |
| Elastic modulus at 300%, kg/cm$^2$ | 44 | 45 | 47 | 21 | 36 |
| Tensile strength at 100° C., kg/cm$^2$ | 40 | 41 | 43 | 16 | 31 |
| Elastic modulus at 100% at 100° C., kg/cm$^2$ | 20 | 22 | 25 | 6 | 18 |
| Permanent compression set, % | 37 | 37 | 33 | 66 | 39 |
| Akron abrasion, % | 164 | 137 | 141 | 397 | 189 |

EXAMPLE 5

Rubber compositions No. 6 to No. 17 were prepared each in the same formulation as in Example 4 except that the kind and amount of the tetrasulfide linkage-containing organosilicon compound were as follows. Namely, the rubber compositions No. 6, No. 7 and No. 8 were admixed with 1, 4 and 8 parts, respectively, of the organosilicon compound prepared in Example 1, the rubber compositions No. 9, No. 10 and No. 11 were admixed with 1, 4 and 8 parts, respectively, of the organosilicon compound prepared in Example 2, the rubber compositions No. 12, No. 13 and No. 14 were admixed with 1, 4 and 8 parts, respectively, of the organosilicon compound prepared in Example 3 and the rubber compositions No. 15, No. 16 and No. 17 were admixed with 1, 4 and 8 parts, respectively, of the same organosilicon compound as used in the rubber composition No. 5 for comparative purpose.

Table 2 below shows the Mooney viscosity of the rubber compositions before vulcanization and the mechanical properties of the vulcanizates obtained by the vulcanization of the compositions at 160° C. for 20 minutes.

TABLE 2

| Rubber composition No. | 6 | 7 | 8 | 9 | 10 | 11 | 12 | 13 | 14 | 15 | 16 | 17 |
|---|---|---|---|---|---|---|---|---|---|---|---|---|
| Mooney viscosity $ML_{1+4}$, minutes | 47 | 19 | 15 | 47 | 19 | 14 | 53 | 28 | 18 | 54 | 33 | 23 |
| Hardness, JIS | 49 | 57 | 62 | 50 | 57 | 62 | 50 | 57 | 61 | 50 | 57 | 61 |
| Ultimate elongation, % | 611 | 535 | 400 | 603 | 511 | 398 | 608 | 532 | 407 | 597 | 465 | 388 |
| Tensile strength, kg/cm$^2$ | 82 | 126 | 185 | 84 | 131 | 188 | 79 | 122 | 176 | 63 | 110 | 154 |
| Tear strength, kg/cm | 24 | 35 | 57 | 24 | 37 | 61 | 24 | 36 | 58 | 22 | 31 | 42 |
| Elastic modulus at 100%, kg/cm$^2$ | 11 | 21 | 88 | 12 | 23 | 91 | 11 | 20 | 76 | 11 | 18 | 34 |

TABLE 2-continued

| Rubber composition No. | 6 | 7 | 8 | 9 | 10 | 11 | 12 | 13 | 14 | 15 | 16 | 17 |
|---|---|---|---|---|---|---|---|---|---|---|---|---|
| Elastic modulus at 300%, kg/cm² | 28 | 62 | 110 | 28 | 65 | 114 | 29 | 61 | 107 | 27 | 49 | 75 |
| Elastic resilience, % | 48 | 52 | 53 | 48 | 52 | 54 | 49 | 53 | 55 | 47 | 50 | 51 |
| Permanent compression set, % | 49 | 33 | 31 | 49 | 34 | 32 | 47 | 30 | 27 | 49 | 38 | 36 |

EXAMPLE 6

Rubber compositions No. 18 to No. 30 were prepared each by uniformly blending, on a 6-inch roller mill, 100 parts of a styrene-butadiene synthetic rubber (SBR 1502, a product by Japan Synthetic Rubber Co.), 50 parts of a precipitated silica filler (Nipsil VN-3, a product by Nippon Silica Co.), 1 part of sulfur, 2 parts of diethylene glycol, 10 parts of the same process oil as used in Example 4, 2 parts of zinc oxide, 2 parts of stearic acid, 1.2 parts of N-hydroxydiethylene-2-benzothiazole sulfenamide, 1.2 parts of dibenzothiazolyl sulfide and 1.0 part of diphenyl guanidine together with (rubber compositions No. 18 to No. 29) or without (rubber composition No. 30) a polysulfide linkage-containing organosilicon compound as mentioned below. Namely, the rubber compositions No. 18, No. 19 and No. 20 were admixed with 1, 2 and 4 parts, respectively, of the organosilicon compound prepared in Example 1, the rubber compositions No. 21, No. 22 and No. 23 were admixed with 1, 2 and 4 parts, respectively, of the organosilicon compound prepared in Example 2, the rubber compositions No. 24, No. 25 and No. 26 were admixed with 1, 2 and 4 parts, respectively, of the organosilicon compound prepared in Example 3 and the rubber compositions No. 27, No. 28 and No. 29 were admixed with 1, 2 and 4 parts, respectively, of the same organosilicon compound as used in the rubber composition No. 5 for comparative purpose.

Table 3 below shows the Mooney viscosity of the rubber compositions before vulcanization and the mechanical properties of the vulcanizates obtained by the vulcanization of the compositions at 160° C. for 20 minutes.

TABLE 3

| Rubber composition No. | 18 | 19 | 20 | 21 | 22 | 23 | 24 | 25 | 26 | 27 | 28 | 29 | 30 |
|---|---|---|---|---|---|---|---|---|---|---|---|---|---|
| Mooney viscosity $ML_{1+4}$, minutes | 71 | 56 | 52 | 73 | 57 | 53 | 70 | 54 | 48 | 76 | 58 | 54 | 98 |
| Hardness, JIS | 64 | 65 | 67 | 64 | 65 | 66 | 65 | 67 | 67 | 64 | 66 | 67 | 64 |
| Ultimate elongation, % | 740 | 530 | 340 | 748 | 545 | 352 | 741 | 527 | 338 | 735 | 518 | 316 | 860 |
| Tensile strength, kg/cm² | 172 | 192 | 161 | 170 | 191 | 158 | 186 | 202 | 173 | 168 | 180 | 151 | 143 |
| Tear strength, kg/cm | 49 | 58 | 58 | 48 | 57 | 58 | 51 | 63 | 65 | 48 | 56 | 58 | 33 |
| Elastic modulus at 100%, kg/cm² | 16 | 26 | 49 | 16 | 25 | 45 | 18 | 27 | 55 | 15 | 25 | 38 | 11 |
| Elastic modulus at 300%, kg/cm² | 36 | 84 | 144 | 34 | 80 | 131 | 38 | 91 | 162 | 29 | 77 | 126 | 20 |
| Elastic resilience, % | 48 | 50 | 52 | 48 | 50 | 51 | 50 | 52 | 53 | 47 | 49 | 51 | 45 |
| Permanent compression set, % | 37 | 22 | 21 | 39 | 24 | 22 | 34 | 20 | 19 | 38 | 24 | 22 | 60 |

EXAMPLE 7

Rubber compositions No. 31 to No. 35 were prepared each by uniformly blending, on a 6-inch roller mill, 100 parts of a terpolymeric synthetic rubber of ethylene, propylene and a diene monomer (EPT 3405, a product by Mitsui Petrochemical Co.), 50 parts of a precipitated silica filler (Nipsil VN-3, supra), 1.5 parts of sulfur, 10 parts of a process oil (R-1000, a product by Kyodo Petroleum Co.), 5 parts of zinc oxide, 1 part of stearic acid, 1 part of 2-mercaptobenzothiazole and 1.5 parts of tetramethyl thiuram monosulfide together with 2.5 parts of the tetrasulfide linkage-containing organosilicon compounds prepared in Examples 1, 2 and 3 for the rubber compositions No. 31, No. 32 and No. 33, respectively, with 2.5 parts of the same organosilicon compound as used in the rubber composition No. 5 for the rubber composition No. 34 and without such an organosilicon compound for the rubber composition No. 35.

Table 4 below shows the Mooney viscosity of the rubber compositions before vulcanization and the mechanical properties of the vulcanizates obtained by the vulcanization of the compositions at 160° C. for 20 minutes.

TABLE 4

| Rubber composition No. | 31 | 32 | 33 | 34 | 35 |
|---|---|---|---|---|---|
| Mooney viscosity $ML_{1+4}$, minutes | 48 | 50 | 46 | 56 | 81 |
| Hardness, JIS | 70 | 70 | 71 | 70 | 70 |
| Ultimate elongation, % | 420 | 425 | 411 | 403 | 637 |
| Tensile strength, kg/cm² | 84 | 79 | 87 | 63 | 42 |
| Tear strength, kg/cm | 36 | 35 | 37 | 35 | 25 |
| Elastic modulus at 100%, kg/cm² | 38 | 36 | 39 | 25 | 18 |
| Elastic modulus at 300%, kg/cm² | 72 | 68 | 76 | 55 | 27 |
| Tensile strength at 100° C., kg/cm² | 46 | 41 | 48 | 34 | 21 |
| Elastic modulus at 100% at 100° C., kg/cm² | 28 | 26 | 29 | 20 | 14 |
| Elastic resilience, % | 56 | 55 | 57 | 53 | 50 |
| Permanent compression set, % | 68 | 71 | 66 | 75 | 84 |

What is claimed is:

1. An organosilicon compound having two polysulfide linkages in a molecule represented by the general formula $$(R^1O)_3Si-R^2-S_x-R^3-S_x-R^2-Si(OR^1)_3,$$

in which $R^1$ is an alkyl group having from 1 to 4 carbon atoms, $R^2$ is a divalent hydrocarbon group having from 1 to 10 carbon atoms, $R^3$ is a divalent hydrocarbon group having from 2 to 10 carbon atoms or a divalent hydrocarbon group additionally containing one or more of the linking units of the formula —O— or —CO—O— in the structure and x is a positive integer of from 2 to 6.

2. The organosilicon compound as claimed in claim 1 wherein the alkyl group denoted by R is a methyl group or an ethyl group.

3. The organosilicon compound as claimed in claim 1 wherein the divalent hydrocarbon group denoted by $R^2$ is a propylene group of the formula —CH$_2$CH$_2$CH$_2$—.

4. The organosilicon compound as claimed in claim 1 wherein the divalent group denoted by $R^3$ is selected from the class consisting of the groups expressed by the formulas
—CH$_2$CH$_2$OCH$_2$CH$_2$OCH$_2$CH$_2$—, —CH$_2$CH$_2$CO—O —CH$_2$CH$_2$—O—COCH$_2$CH$_2$— and —CH$_2$CH=CHCH$_2$—.

5. The organosilicon compound as claimed in claim 1 wherein the subscript x is 4.

6. A method for the preparation of an organosilicon compound having two polysulfide linkages in a molecule represented by the general formula $(R^1O)_3Si-R^2-S_x-R^3-S_x-R^2-Si(OR^1)_3$, in which $R^1$ is an alkyl group having from 1 to 4 carbon atoms, $R^2$ is a divalent hydrocarbon group having from 1 to 10 carbon atoms, $R^3$ is a divalent hydrocarbon group having from 2 to 10 carbon atoms or a divalent hydrocarbon group additionally containing one or more of the linking units of the formula —O— or —CO—O— in the structure and x is a positive integer of from 2 to 6, which comprises:

(a) reacting a mercaptoalkyl trialkoxy silane of the formula $(R^1)_3SiR^2SH$ with sulfur chloride to form a compound of the formula $(R^1O)_3SiR^2S_{x-1}Cl$; and (b) subjecting the compound $(R^1O)_3SiR^2S_{x-1}Cl$ to a dehydrochlorination reaction with a dimercaptan compound of the formula HS—$R^3$—SH.

7. A method for the preparation of an organosilicon compound having two polysulfide linkages in a molecule represented by the general formula $(R^1O)_3Si-R^2-S_x-R^3-S_x-R^2-Si(OR^1)_3$, in which $R^1$ is an alkyl group having from 1 to 4 carbon atoms, $R^2$ is a divalent hydrocarbon group having from 1 to 10 carbon atoms, $R^3$ is a divalent hydrocarbon group having from 2 to 10 carbon atoms or a divalent hydrocarbon group additionally containing one or more of the linking units of the formula —O— or —CO—O— in the structure and x is a positive integer of from 2 to 6, which comprises: (a) reacting a chloroalkyl trialkoxy silane of the formula $(R^1O)_3SiR^2Cl$ and sodium sulfide of the formula $Na_2S_x$ to form a compound of the formula $(R^1O)_3SiR^2S_xNa$; and (b) reacting the compound $(R^1O)_3SiR_2S_xNa$ with a dihalide compound of the formula X—$R^3$—X, in which X is a halogen atom.

* * * * *

UNITED STATES PATENT AND TRADEMARK OFFICE
CERTIFICATE OF CORRECTION

PATENT NO. : 4,709,065

DATED : November 24, 1987

INVENTOR(S) : Hiroshi Yoshioka; Ichiro Ono; Hitoshi Uehara

It is certified that error appears in the above-identified patent and that said Letters Patent is hereby corrected as shown below:

Claim 2, column 11, line 4, the formula "R" should read -- $R^1$ --.

Claim 6, column 12, line 4, the formula reading "$(R^1)_3SiR^2SH$" should read -- $(R^1O)_3SiR^2SH$ --.

Signed and Sealed this

First Day of November, 1988

Attest:

DONALD J. QUIGG

Attesting Officer

Commissioner of Patents and Trademarks